US006934574B1

(12) United States Patent
Damadian et al.

(10) Patent No.: US 6,934,574 B1
(45) Date of Patent: Aug. 23, 2005

(54) MRI SCANNER AND METHOD FOR MODULAR PATIENT HANDLING

(75) Inventors: Jevan Damadian, East Northport, NY (US); John Linardos, Smithtown, NY (US)

(73) Assignee: Fonar Corporation, Melville, NY (US)

( * ) Notice: Subject to any disclaimer, the term of this patent is extended or adjusted under 35 U.S.C. 154(b) by 469 days.

(21) Appl. No.: 10/175,999

(22) Filed: Jun. 20, 2002

Related U.S. Application Data (60) Provisional application No. 60/326,365, filed on Oct. 1, 2001, provisional application No. 60/299,880, filed on Jun. 21, 2001.

(51) Int. Cl.[7] .................................................. A61B 5/05
(52) U.S. Cl. .................................................... 600/415
(58) Field of Search ..................... 600/415, 411, 410, 600/407; 324/306, 307, 308, 309

(56) References Cited

U.S. PATENT DOCUMENTS

| | | | |
|---|---|---|---|
| 4,534,358 A | 8/1985 | Young | 128/653 |
| 4,608,991 A | 9/1986 | Rollwitz | 128/653 |
| 4,613,820 A | 9/1986 | Edelstein et al. | 324/318 |
| 4,629,989 A | 12/1986 | Riehl et al. | 324/318 |
| 4,651,099 A | 3/1987 | Vinegar et al. | 324/320 |
| 4,668,915 A | 5/1987 | Daubin et al. | 324/309 |
| 4,707,663 A | 11/1987 | Minkoff et al. | 324/319 |
| 4,766,378 A * | 8/1988 | Danby et al. | 324/307 |
| 4,777,464 A | 10/1988 | Takabatashi et al. | 335/306 |
| 4,805,626 A * | 2/1989 | DiMassimo et al. | 600/415 |
| 4,829,252 A | 5/1989 | Kaufman | 324/309 |
| 4,875,485 A | 10/1989 | Matsutani | 128/653 |
| 4,968,937 A | 11/1990 | Akgun | 324/318 |
| 4,985,678 A | 1/1991 | Gangarosa et al. | 324/318 |
| 5,008,624 A | 4/1991 | Yoshida | 324/318 |
| 5,061,897 A | 10/1991 | Danby et al. | 324/318 |
| 5,065,761 A | 11/1991 | Pell | 128/660.03 |
| 5,122,363 A | 6/1992 | Balkus, Jr. et al. | |
| 5,124,651 A | 6/1992 | Danby et al. | 324/318 |
| 5,128,121 A | 7/1992 | Berg et al. | |
| 5,153,546 A | 10/1992 | Laskaris | 335/216 |
| 5,162,768 A | 11/1992 | McDougall et al. | 335/296 |
| 5,194,810 A | 3/1993 | Breneman et al. | 324/318 |
| 5,197,474 A | 3/1993 | Englund et al. | 128/653.5 |
| 5,207,224 A | 5/1993 | Dickinson et al. | 128/653.5 |
| 5,229,723 A | 7/1993 | Sakurai et al. | 324/319 |
| 5,250,901 A | 10/1993 | Kaufman et al. | 324/318 |
| 5,291,890 A | 3/1994 | Cline et al. | 128/653.2 |
| 5,305,749 A | 4/1994 | Li et al. | 128/653.2 |

(Continued)

OTHER PUBLICATIONS

Niendorf, H P., et al., "Safety and tolerance after intravenous administration of 0.3 mmol/kg Gd-DTPA. Results of a randomized, controlled clinical trial.", *Investigative Radiology, 26 Suppl 1*, S221-3; discussion S232-5,(1991),S221-5.

(Continued)

*Primary Examiner*—Daniel Robinson
(74) *Attorney, Agent, or Firm*—Schwegman, Lundberg, Woessner & Kluth, P.A.

(57) ABSTRACT

An MRI scanner that includes a magnet with poles having substantially vertical pole surfaces and a removable positioner for supporting a patient within a gap in the pole surfaces. A method of positioning a patient within a gap formed by vertical pole surfaces in an MRI scanner. The method includes selecting a first patient positioner and inserting the first patient positioner into the gap between vertical pole surfaces in the MRI scanner.

14 Claims, 7 Drawing Sheets

U.S. PATENT DOCUMENTS

| | | | |
|---|---|---|---|
| 5,315,276 A | 5/1994 | Huson et al. | 335/216 |
| 5,382,904 A | 1/1995 | Pissanetzky | 324/319 |
| 5,412,363 A | 5/1995 | Breneman et al. | 335/216 |
| 5,423,315 A * | 6/1995 | Margosian et al. | 600/410 |
| 5,436,607 A | 7/1995 | Chari et al. | 335/216 |
| 5,460,799 A | 10/1995 | Elgavish et al. | |
| 5,490,513 A | 2/1996 | Damadian et al. | 128/653.2 |
| 5,519,372 A | 5/1996 | Palkovich et al. | 335/216 |
| 5,592,090 A | 1/1997 | Pissanetzky | 324/319 |
| 5,606,970 A | 3/1997 | Damadian | 128/653.2 |
| 5,697,164 A | 12/1997 | Hausmann et al. | |
| 5,735,278 A | 4/1998 | Hoult et al. | 128/653.2 |
| 5,779,637 A * | 7/1998 | Palkovich et al. | 600/415 |
| 5,899,859 A | 5/1999 | Votruba et al. | |
| 6,011,396 A | 1/2000 | Eckels et al. | |
| 6,141,579 A * | 10/2000 | Bonutti | 600/415 |
| 6,236,210 B1 | 5/2001 | Takekoshi et al. | |
| 6,278,274 B1 | 8/2001 | Biglieri et al. | |
| 6,311,082 B1 * | 10/2001 | Creighton et al. | 600/407 |
| 6,345,193 B2 | 2/2002 | Dutto et al. | |
| 6,377,830 B1 | 4/2002 | Carrozzi et al. | |
| 6,385,481 B2 * | 5/2002 | Nose et al. | 600/415 |
| 6,504,371 B1 | 1/2003 | Damadian et al. | |
| 2001/0012914 A1 | 8/2001 | Kuth et al. | 600/415 |

OTHER PUBLICATIONS

Oldendorf, William H., et al., "Brain extracellular space and the sink action of cerebrospinal fluid", *Archives of Neurology, 17*, (1967), 196-205.

* cited by examiner

MRI SCANNER AND METHOD FOR MODULAR PATIENT HANDLING

CROSS-REFERENCES TO RELATED APPLICATIONS

This application claims priority to co-assigned U.S. Provisional Application Ser. No. 60/299,880 filed Jun. 21, 2001, U.S. patent application Ser. No. 09/918,369 filed Jul. 30, 2001, and U.S. Provisional Application Ser. No. 60/326,365 filed Oct. 1, 2001, which applications are incorporated herein by reference.

FIELD OF THE INVENTION

This invention relates to MRI scanners, and more specifically to an MRI scanner and method with modular patient handling.

BACKGROUND

Patient positioning is critical in order for medical personnel to properly treat and/or diagnose patients. One example is in magnetic resonance imaging (MRI) where a portion of the patient's anatomy is scanned within a relatively small imaging volume in an MRI scanner.

One type of MRI scanner includes a magnet that is formed with two poles. A patient is positioned in a gap between the poles during a scanning procedure.

Figure 1:
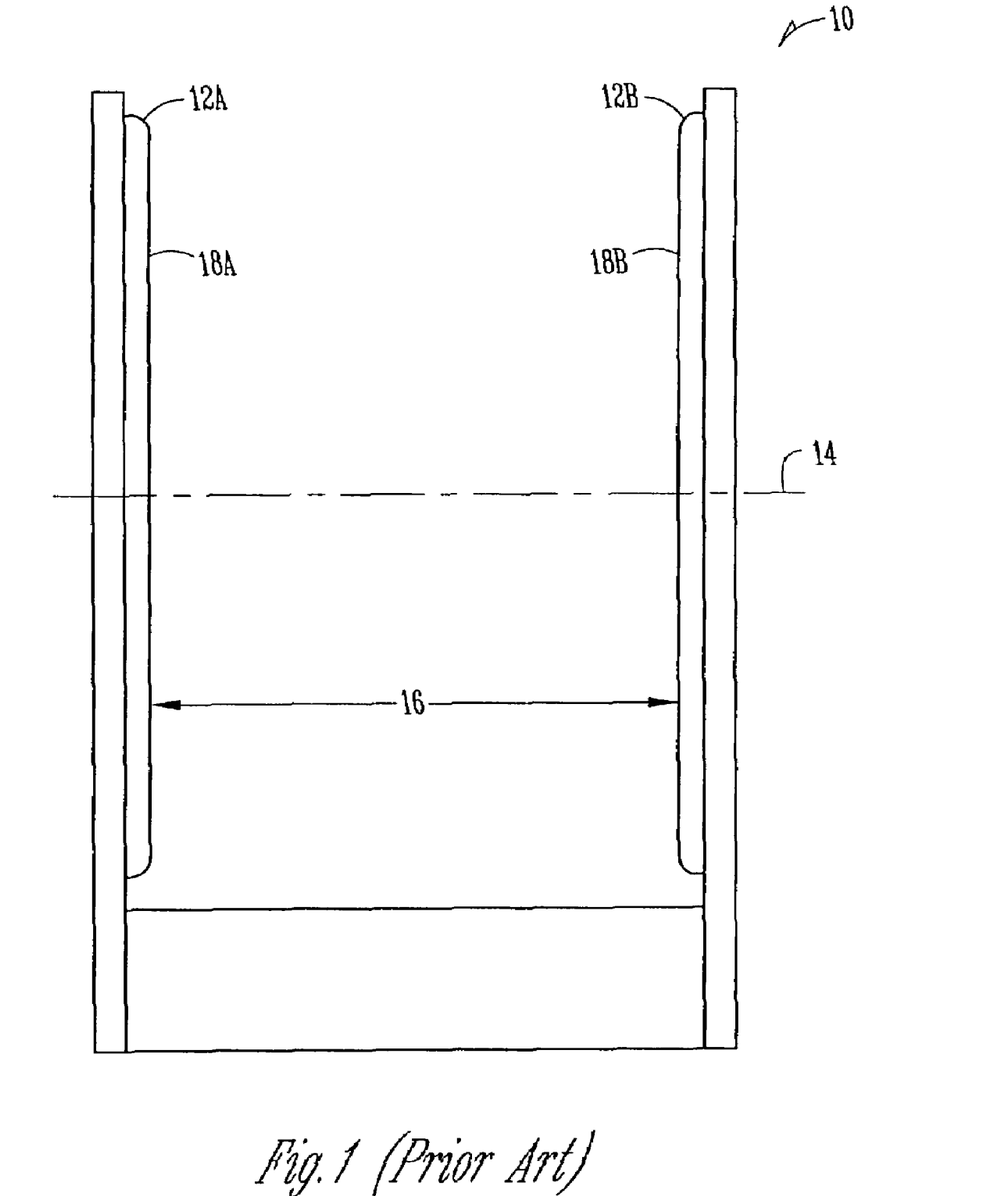
FIG. 1 shows an end view illustrating a portion of a prior art MRI scanner.

A prior art MRI scanner is shown in FIG. 1. The scanner 10 includes two poles 12A, 12B. The pole 12A, 12B are oriented along a common horizontal pole axis 14 such that a gap 16 is formed between vertical pole surfaces 18A, 18B on poles 12A, 12B. A patient positioner (not shown) is positioned within the gap 16. During a scanning operation a patient is placed onto the patient positioner.

One problem with MRI scanner 10 is that patients are often oriented with their body in a horizontal position. However, there are times when other positions of the body, such as vertical, angular, Trendelenburg and/or reverse Trendelenburg, are desirable to appropriately diagnosis or treat a patient.

Another problem is that the patient positioner within the gap is fixed such that using multiple different types of positioners is impractical. Since any one patient positioner is typically limited in how it can orient a patient within the gap, the ability to quickly and accurately maneuver a patient into an appropriate position may be compromised depending on how a patient needs to be scanned. Many of the fixed positioners have limited ability to orient a patient in a number of positions.

SUMMARY

The present invention relates to an MRI scanner that provides for fast and accurate patient positioning. The MRI scanner includes a magnet with substantially vertical pole surfaces and a removable positioner for supporting a patient within a gap between the pole surfaces.

The removable positioner makes the MRI scanner modular such that one or more removable positioners may be used to support a patient within the vertical gap in the magnet. The one or more positioners may include, but are not limited to, a horizontal/Trendelenburg bed, a stand-up/sit-down bed, a horizontally movable track, and a walk-through positioner. In one example embodiment, an elevator is located in the floor beneath the gap in the magnet to allow the patient to be moved up and down into the appropriate position within the magnet. Other embodiments include different types of removable patient positioners, such as a treadmill located within the floor beneath the magnet gap and/or one or more removable gates rotatably coupled to the floor or an elevator platform beneath the gap.

The modular nature of the MRI scanner allows any type of removable positioner to be inserted into the vertical gap depending on a patient's scanning needs. In addition, the MRI scanner provides a universal approach to patient positioning that allows a patient to be positioned in an appropriate position with one or more easy to manufacture and remove patient positioners.

The present invention also relates to a method of positioning a patient within a gap formed by vertical pole surfaces in an MRI scanner. The method includes selecting a first patient positioner and inserting the first patient positioner into the gap between vertical pole surfaces in the MRI scanner.

In an example embodiment, the first patient positioner is inserted into the gap is a transportable patient bed that is removably positioned within the gap in the magnet. The transportable patient bed may include a support platform that can be positioned in a range of orientations, such as horizontal and Trendelenburg. In an alternative form, the patient bed includes a back rest portion rotatably attached to a base and a lower section rotatably attached to the base.

DETAILED DESCRIPTION

The following detailed description and figures describe and illustrate one or more specific embodiments of the invention. These embodiments are shown and described in sufficient detail to enable those skilled in the art to practice the invention.

The present invention relates to an MRI scanner with a magnet having a horizontal magnetic field. The MRI scanner provides various means for positioning a patient in the vertical gap between two magnet poles. The MRI scanner includes a variety of patient positioners that are removably mounted within the gap to support a patient during a scanning procedure. The modular nature of the MRI scanners allows the various removable positioners to be exchanged for one another quickly and easily depending on the type of scan that needs to be performed.

Figure 2A:
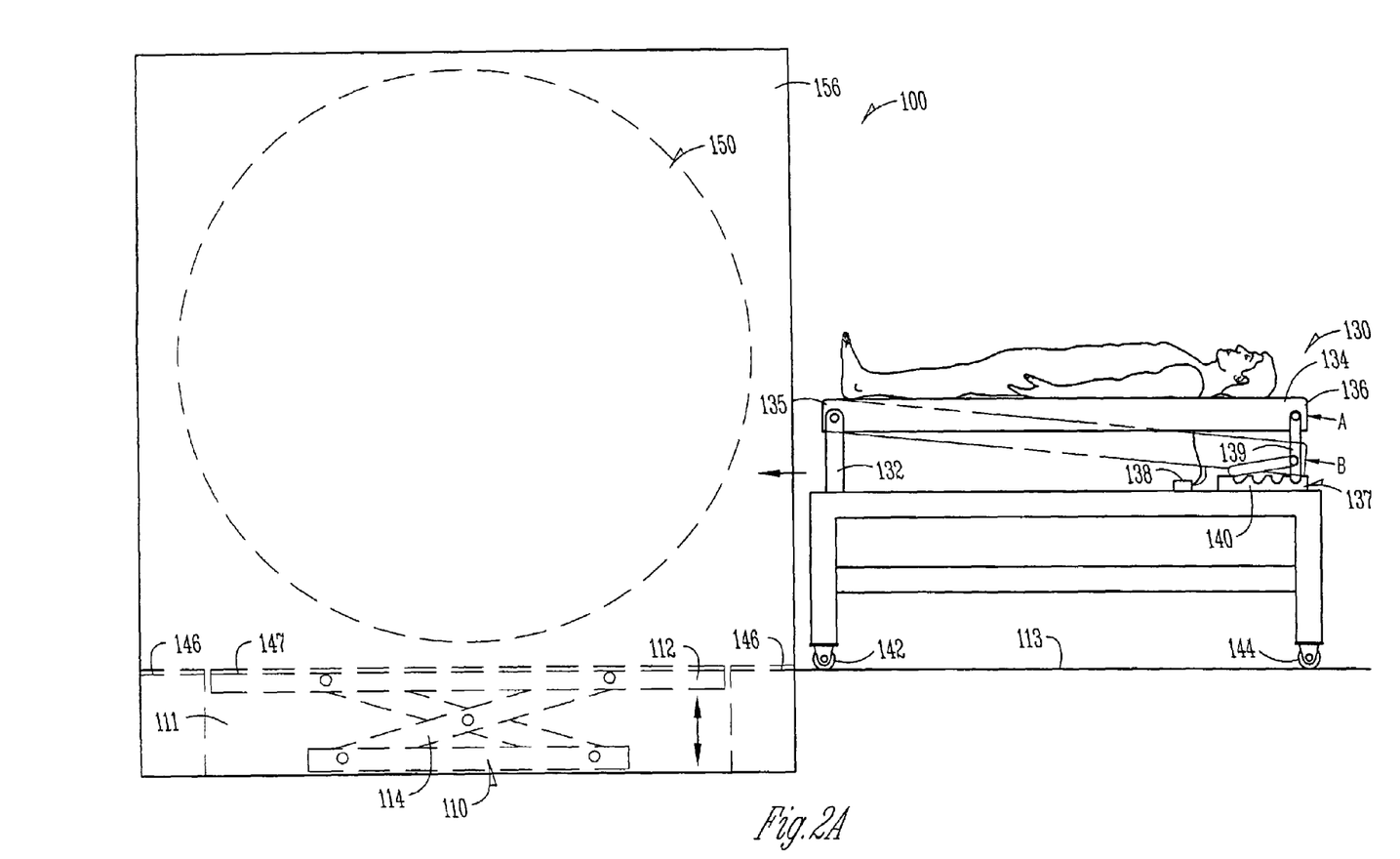
FIG. 2A shows a front view illustrating a portion of an MRI scanner according to one embodiment of the present invention.
Figure 2B:
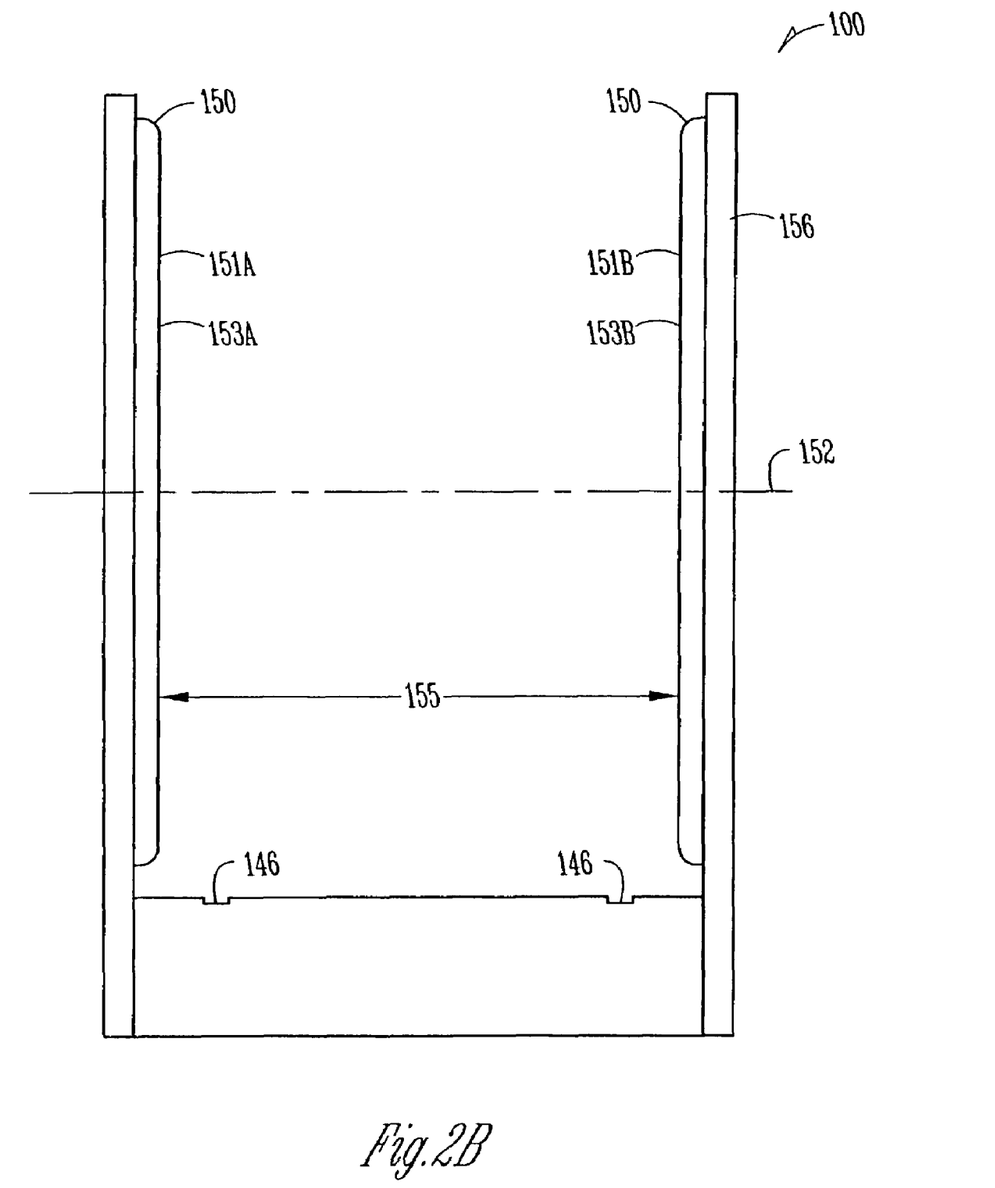
FIG. 2B shows an end view of the MRI scanner illustrated in FIG. 2A.

FIGS. 2A and 2B show an MRI scanner 100 according to one embodiment of the present invention. Scanner 100 includes one or more removable positioners that are able to articulate a patient's anatomy in various orientations and heights in order to perform scanning procedures. One of the removable positioners that may be used in scanner 100 is an elevator 110. Another of the removable positioners is a transportable patient bed 130. Elevator 110 and patient bed 130 can be used singularly or in combination to position a patient for a scanning procedure.

MRI scanner includes a magnet 150. Magnet 150 includes a pair of opposed poles 151A, 151B that are aligned along a horizontally oriented pole axis 152. The poles 151A, 151B include surfaces 153A, 153B that define a gap 155. A patient is inserted into gap 155 between poles 151A, 151B in order to perform a scanning procedure. The pole axis may be anywhere from 3 to 6 feet above the floor, although in other embodiments pole axis 152 may less than 3 feet and greater than 6 feet without departing from the scope of the present invention. Poles are mounted on a frame 156. In alternative embodiments (not shown), the source of magnetic energy may come from permanent magnets, superconducting coils or resistive electrical coils that are in close proximity to portions of a frame.

Elevator 110 is located within a hole 111 in a floor 113 that supports a portion 100 of an MRI scanner. Elevator 110 includes a support platform 112 which is raised and lowered by a scissor mechanism 114. Scissor mechanism 114 may be driven by a motor, such as a servo-motor, a screw lift, hydraulic lift, or any other equivalent mechanical or electromechanical lift mechanism. Elevator 110 may include an encoder or any other means for sensing and controlling the height of elevator 110 relative to magnet 150.

During operation of the scanner, elevator 110 moves patient bed 130 up and down relative to magnet 150 depending the portion of a patient's anatomy that needs to be scanned. When a patient bed is not vertically adjustable, it may be difficult for medical personnel to appropriately position a patient within magnet 150. Therefore, elevator 110 is especially effective when used in conjunction with patient beds that are not vertically adjustable.

Elevator 110 may also be used with different beds described below or without a patient bed. A patient may stand directly on support platform 112 or another positioner demonstrating the modular positioning flexibility of scanner 100. In some embodiments, elevator 110 is omitted and one or more other removable positioners described herein are included in a scanner of the present invention:

Patient bed 130 is one example of a bed that may be used for horizontal or Trendelenburg positioning of a patient within MRI scanner 100. In the illustrated example embodiment, patient bed 130 includes a frame 132 and a platform 134. Patient bed 130 fits within gap 155 and may be a light-weight hospital-type bed manufactured from nonmagnetic material such as PVC, G10, wood, or other material. Platform 134 may include a cushioned surface, such as a pad, mat or mattress. A first end 135 of platform 134 is rotatably attached to one end of frame 132 while a second end 136 of platform 134 is attached to a mechanism 137 that raises and lowers second end 136 relative to frame 132. Platform 134 may be put into a horizontal position A, a Trendelenburg position B, or any position in between. If a patient is placed onto the bed with their head and feet in a reverse orientation, the patient may be maneuvered into a reverse Trendelenburg position.

In the illustrated example embodiment, mechanism 137 is a "lawn-chair" type mechanism that includes a support member 139 rotatably attached to second end 136 of platform 134 and a stop member 140 with grooves that receive support member 139. Positioning support member 139 in different grooves on stop member 140 adjusts the angle of platform 134 relative to frame 132. Other lifting mechanisms may be used without departing from the scope of the present invention.

Patient bed 130 may also include one or more bed angle sensors 138 that provide data to a controller (not shown) relating to the angle of platform 134. Based on the data received from sensor 138, controller can establish the angle of platform 134 and/or provide information as to the orientation of an MRI image during or after a scan.

Patient bed 130 includes a first set of wheels 142 and a second set of wheels 144. Wheels 142, 144 are located at the bottom of the frame 132 and are used to roll patient bed 130 across floor 113 into and out of MRI scanner 100. In some embodiments, first wheels 142 are fixed while second wheels 144 are able to rotate. One, or both, sets of wheels 142, 144 may be coupled to a drive motor that is used to propel patient bed 130.

In the illustrated embodiment, wheels 142 and 144 ride within grooves 146 in floor 113. Grooves 146 may run all, or part way, through the room where scanner 110 is located. The grooves preferably extend through gap 155 such that grooves 146 guide patient bed 130 throughout the scanning procedure. When portion 100 of the scanner includes elevator 110, support platform 112 may include grooves 147 that are aligned with grooves 146 in floor 113. Grooves 146, 147 are superior to obstacles, such as raised tracks or rails, for guiding a patient beds because raised obstacles can hinder patients or medical personnel during a scanning procedure.

Patient bed 130 may further include removable shoulder supports (not shown) that can be attached to platform 134. The shoulder supports may be padded or cushioned to provide comfortable support to a patient's shoulders when the patient is oriented in the Trendelenburg position.

In other embodiments, patient bed 130 includes RF connection ports (not shown) that communicate data with a receiver which is part of a control system. RF ports may be connected to various portions of patient bed 130 including adjustment controls, power supplies and switches.

Patient bed 130 may also include one or more connection mechanisms such as dove-tailed or keyed slots that provide a location for attaching auxiliary equipment to patient bed 130. Some examples of auxiliary equipment include surface coils, cine fixtures, calibration equipment, patient restraints and patient seating.

During operation of scanner 100, a trained operator enters information into a controller, such as a computer. The computer can be located within the same room as scanner 100 or in another room. The operator may enter a variety of information, including but not limited to (i) whether the scan is to be a horizontal, tilt, stand-up, seated or substantially vertical scan; and (ii) the type of positioner to be utilized.

Patient bed 130 is wheeled into gap 155 and elevator 110 is raised or lowered if necessary to perform a scan. Patient bed 130 may be inserted from a front side of magnet 150 and wheeled out a back side of magnet 150 to promote efficient use of scanner 100. The modular nature of scanner 100 allows any one of a number of removable positioners to be inserted between poles 151A, 151B of magnet 150.

Figure 3:
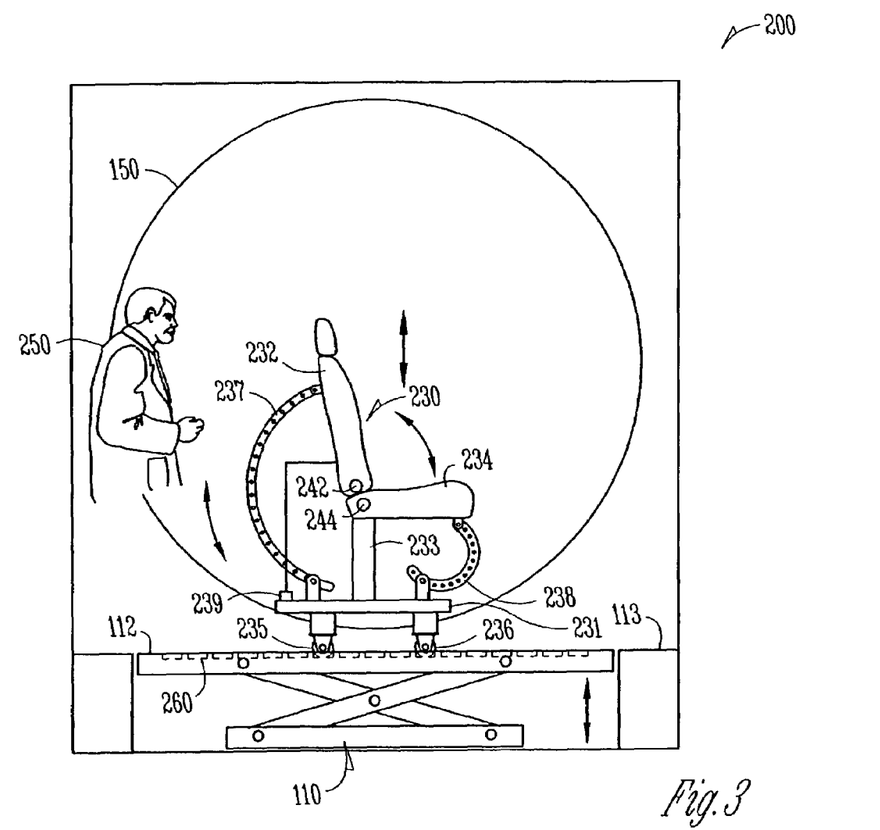
FIG. 3 shows a front view illustrating a portion of an MRI scanner according to another embodiment of the present invention.

FIG. 3 illustrates a portion 200 of an MRI scanner according to another embodiment of the present invention. In the illustrated embodiment, portion 200 similarly includes elevator 110 and another type of removable patient positioner 230, that is adapted to be inserted into the vertical gap between the poles that form magnet 150. Magnet 150 and elevator 110 are as described above.

Removable patient positioner 230 is a stand-up, sit-down, lie-down patient positioner. Removable patient positioner 230 includes a base 231, a back rest portion 232 and a lower section 234. Sets of wheels 235, 236 are attached to a bottom surface of base 231 to roll removable patient positioner 230 across floor 113 into and out of MRI scanner 200. As described above, a drive motor may be coupled to one or both sets of wheels 235 or 236 in order to propel removable patient positioner 230.

In an example embodiment, a top surface of support platform 112 on elevator 110 includes perpendicular notches 260 that are adapted to receive wheels 235, 236. The perpendicular notches 260 prevent the removable patient positioner 230 from inadvertently rolling when removable patient positioner 230 is positioned within magnet 150.

Back rest portion 232 is rotatably attached via a hinged portion 242 to a projection 233 that extends up from base 231 A locking mechanism 237 allows back rest portion 232 to be set at a variety of angles such that a patient may be positioned in a stand-up or a lie-down (recumbent) position, or any angle in between.

Lower section 234 is also rotatably attached via a hinged portion 244 to projection 233. A locking mechanism 238 secures lower section 234 at any appropriate angle for scanning. As described above, one or more sensors 239 may be incorporated into removable patient positioner 230 to provide data to a control system relating to the angle of back rest 232 and/or lower portion 234.

Figure 4:
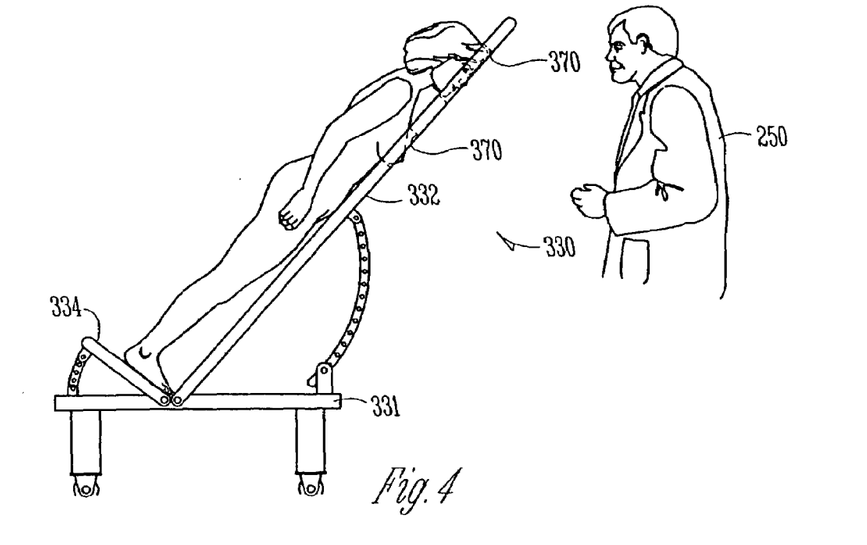
FIG. 4 shows an alternative removable patient positioner that may be used in the MRI scanner illustrated in FIG. 3.
Figure 8:
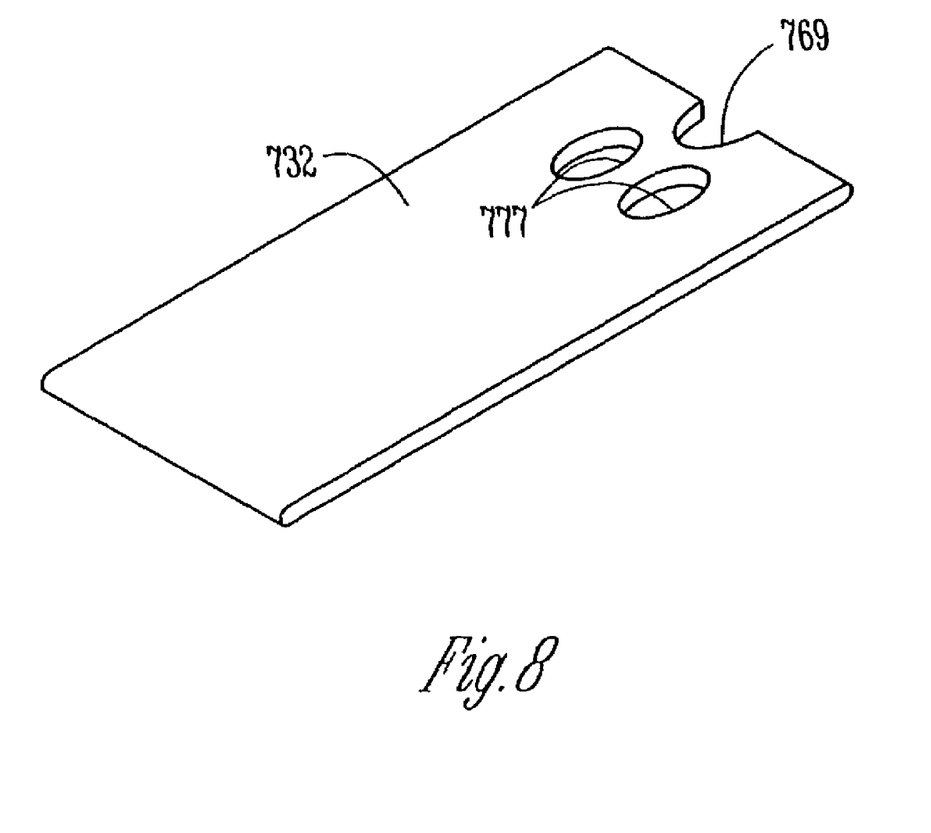
FIG. 8 shows an alternative backrest portion that may be used in the removable patient positioner illustrated in FIG. 4.

FIG. 4 illustrates a patient bed 330 that could also be used as a removable positioner in scanner 200. Patient bed 330 is similar to removable patient positioner 230 in that patient bed 330 includes a lower section 334 and a back rest portion 332 that are rotatably connected to a base 331. In this embodiment, lower section 334 and back rest 332 are mounted directly to base 331. The relative lengths of lower section 334 and back rest portion 332 are different such that lower section 334 can serve as a standing platform. Back rest portion 332 may also include one or more openings 370 where portions of a patient's anatomy, such as breasts and/or a head, can extend through back rest portion 332. FIG. 8 shows one example alternative backrest portion 732 that includes openings 777 for breasts and a cutout section 769 for a patient's head.

The adjustability of patient bed 330 provides improved positioning for MRI scanning and MRI-guided surgery. FIGS. 3 and 4 show some example locations where a surgeon 250 may be positioned during MRI-guided surgery. One example adjustment during MRI-guided surgery can be described with reference to FIG. 3. Back rest 232 may adjusted down or up to permit easier access to a patient's head by surgeon 250. Another example adjustment can be described with reference to FIG. 4. In the illustrated embodiment, back rest 332 may be adjusted down or up to permit easier access to a patient's head or breasts by surgeon 250.

Any of the removable positioners described herein may include handles on any portion of the removable positioner to facilitate maneuvering positioners into and out of magnet 150. Any of the features and options described above relative to patient beds 130, 230 may also be incorporated into patient bed 330. The modular nature of scanners 100, 200 allow any one of a number of removable positioners to be placed within magnet 150.

Figure 5:
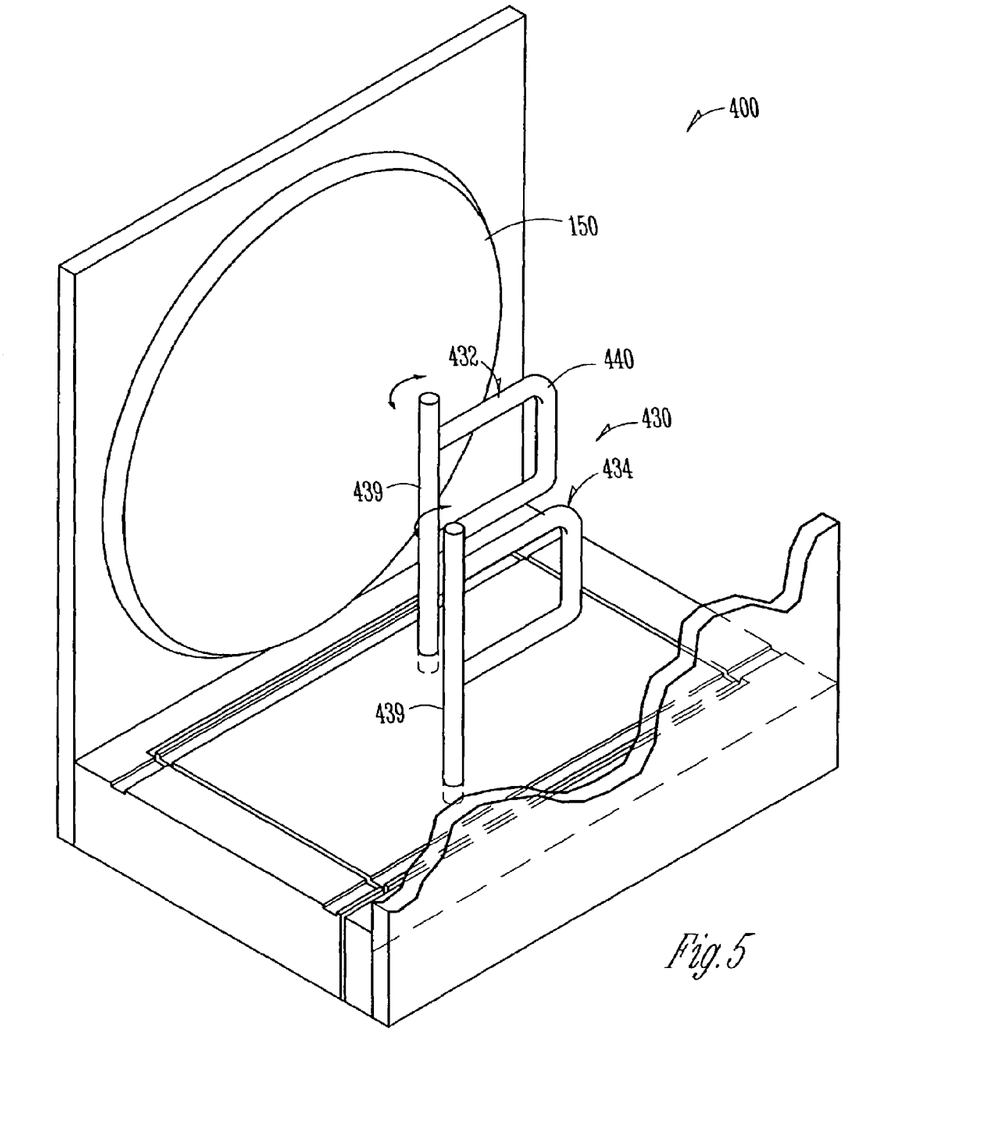
FIG. 5 shows a perspective view of another MRI scanner encompassing the present invention.
Figure 6:
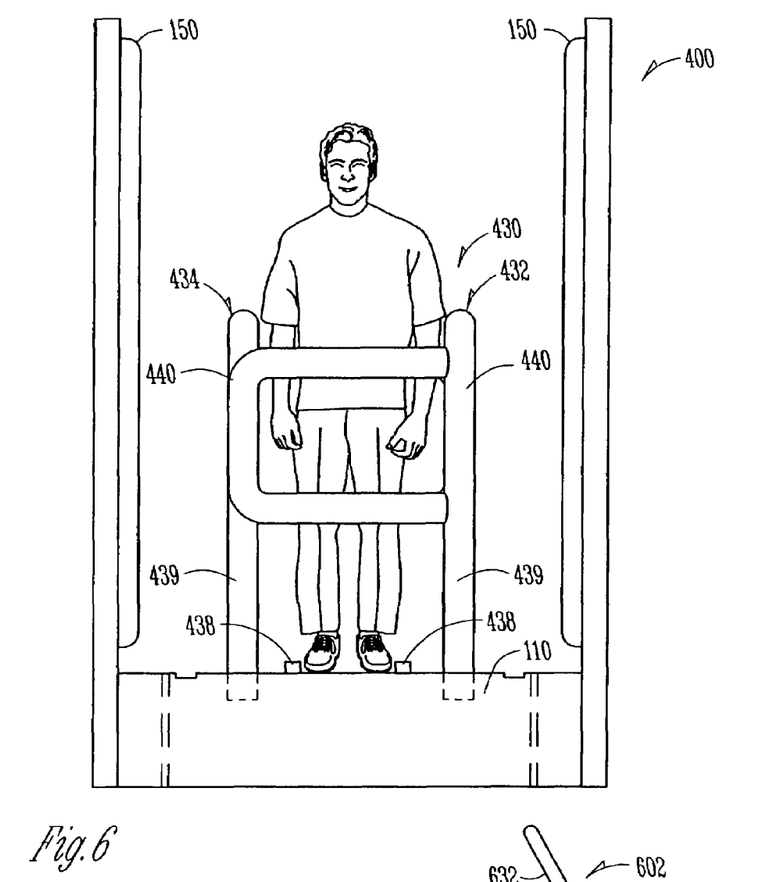
FIG. 6 shows an end view of the MRI scanner illustrated in FIG. 5.

FIGS. 5 and 6 illustrate an MRI scanner 400 according to another example embodiment of the present invention. MRI scanner 400 similarly includes elevator 110 and a removable patient positioner 430 that is adapted to be inserted into the vertical gap in magnet 150.

Patient positioner 430 includes one or more rotatable gates 432, 434. Each gate 432, 434 includes a post portion 439 that is rotatably and removably coupled to elevator 110. An upper portion of each gate 432, 434 includes a support section 440. Depending on the type of scan and the condition of the patient, the patient can lean against the support section 440 on one gate and hold the support section 440 of the other gate during a scanning procedure.

One type of walk-through scan may start with the patient walking past an open entrance gate 432 into magnet 150. Entrance gate 432 closes and the patient leans back against entrance gate 432 using exit gate 434 as a hand rest during the scan. In some embodiments, a foot positioner 438 is removably or permanently located on elevator 110 to properly position the patient. Elevator 110 is used to raise and lower the patient as needed. Exit gate 434 opens when the scan is done and the patient walks out of scanner 400.

Figure 7:
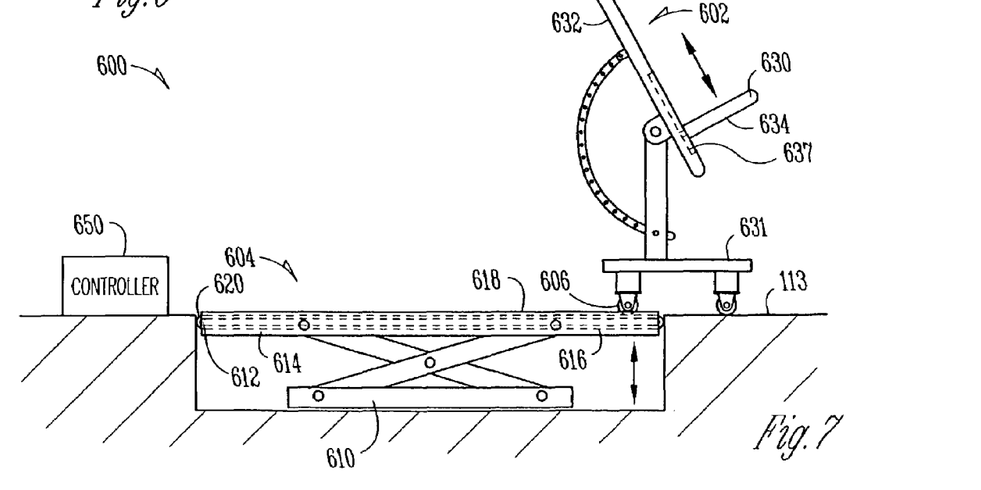
FIG. 7 shows a front view illustrating a portion of another MRI scanner encompassing the present invention.

FIG. 7 shows an MRI scanner 600 according to another embodiment of the present invention. Magnet 150 has been omitted from FIG. 7 for purposes of clarity. Scanner 600 includes a removable patient positioner, such as patient bed 602. Patient bed 602 is similar to removable patient positioner 230 described above. Patient bed 602 similarly includes a base 631, a back rest portion 632, and a lower section, such as a seat 634. In the illustrated embodiment, patient bed 602 includes a locking mechanism 637 such that seat 634 translates along back rest portion 632 to raise and lower a patient positioned on seat 634.

Scanner 600 further includes an elevator 610 and a treadmill 614 mounted above elevator 610. Treadmill 614 includes one or more pulleys 612 and a belt 616 wrapped around pulleys 612. Rails 618 are configured at the level of floor 113 near belt 616 to guide wheels 606 on patient bed 602 as patient bed 602 is moved onto belt 616. Rails 618 prohibit bed 602 from moving laterally when treadmill 614 is activated to move patient bed 602 into and out of scanner 600.

Belt 616 may be operated manually or electrically by a motor. In some embodiments, a controller 650 directs the motor to deliver patient bed 602 to a desired position for an MRI scan. Elevator 610 may then be lowered or raised to perform the desired scan. Scanner 600 may not include an elevator 610 such that treadmill 614 is mounted at the level of floor 113.

The present invention also relates to a method of positioning a patient within a gap 155 formed by vertical pole surfaces 153A, 153B in an MRI scanner 100. The method includes selecting a first patient positioner and inserting the first patient positioner into gap 155 between vertical pole surfaces 153A, 153B. The method may further include removing a second patient positioner from between gap 155 before inserting the first patient positioner. In some embodiments, the method includes inserting the first patient positioner from a front side of MRI scanner 100 and removing the second patient positioner from a back side of MRI scanner 100.

Inserting the first patient positioner into gap 155 may include inserting a plurality of rotatable gates into gap 155 such that a patient can grasp one gate and lean against another gate during a scan. One or more of the gates may be removably inserted into an elevator positioned below gap 155.

In other example embodiments, the method includes adjusting the position of a patient using the first patient positioner. Adjusting the position of a patient can include (i) rotating a platform on the first patient positioner relative to a frame of the first patient positioner by raising and lowering a second end of the platform relative to a first end of the platform; (ii) rotating a back rest portion on the first patient positioner relative to a base on the first patient positioner; (iii) inserting a body part of the patient through an opening in the back rest portion of the first patient positioner; and/or (iv) rotating a lower section of the first patient positioner relative to the base.

In some embodiments, a patient is positioned onto a patient positioner before the patient positioner is positioned within gap 155. The patient can be adjusted on the patient positioner before and/or after insertion into gap 155.

The method may further include sensing the position of one or more parts that make up the first patient positioner and adjusting the first patient positioner based on data received from the sensors.

In some embodiments, the method includes maneuvering wheels on a transportable patient bed within grooves that guide the patient bed in order to position the patient bed in gap 155. The method may further include placing a first patient positioner onto a support platform of an elevator and elevating the first patient positioner by raising the support platform with a scissors mechanism. In one example embodiment, the method includes sensing data relating to the height of the support platform and controlling the height of the elevator based on the data.

The modular nature of the MRI scanners and methods described above allow medical personnel to quickly and easily change between positioners. The ability to quickly change positioners provides a multitude of options for positioning patient that require MRI scans.

It is understood that the above description is intended to be illustrative and not restrictive. Many other embodiments will be apparent to those of skill in the art upon reviewing the above description. The scope of the invention should be determined with reference to the appended claims along with the full scope of equivalents to which the claims are entitled.

What is claimed is:

1. An MRI scanner comprising:
   a magnet including poles having substantially vertical pole surfaces such that there is a gap between the pole surfaces; and
   a removable positioner for supporting a patient within the gap; and
   an elevator positioned below the gap to raise and lower the positioner relative to the poles of the magnet, wherein the elevator includes a support platform and a scissor mechanism that raises and lowers the support platform.

2. An MRI scanner comprising:
   a magnet including poles having substantially vertical pole surfaces such that there is a gap between the pole surfaces; and
   a removable positioner for supporting a patient within the gap; and
   an elevator positioned below the gap to raise and lower the removable positioner relative to the poles of the magnet, wherein the elevator includes a sensor and a control coupled to the sensor to position the height of the elevator.

3. An MRI scanner comprising:
   a magnet including poles having substantially vertical pole surfaces such that there is a gap between the pole surfaces; and
   a removable positioner for supporting a patient within the gap, wherein the removable positioner includes a control and radio frequency (RF) connection ports that exchange signals with the control to orient the removable positioner.

4. An MRI scanner comprising:
   a magnet including poles having substantially vertical pole surfaces such that there is a gap between the pole surfaces; and
   a removable positioner for supporting a patient within the gap wherein the magnet includes a front side and a back side, the gap communicating with the front and back sides of the magnet such that the removable positioner can enter the gap from the front side and the back side of the magnet.

5. An MRI scanner comprising:
   a magnet including poles having substantially vertical pole surfaces such that there is a gap between the pole surfaces; and
   a removable positioner for supporting a patient within the gap, wherein the removable positioner includes a pair of gates, each gate including a support section such that a patient can grasp the support section of one gate and lean against the support section of the other gate.

6. The MRI scanner of claim 5 wherein the removable positioner includes an elevator such that the pair of gates are rotatably mounted on the elevator.

7. A method of positioning a patient within a gap formed by vertical pole surfaces in an MRI scanner, the method comprising:
   selecting a first patient positioner;
   inserting the first patient positioner into the gap between the vertical pole surfaces; and
   removing a second patient positioner from between the gap before inserting the first patient positioner into the gap, wherein inserting the first patient positioner into the gap between the vertical pole surfaces includes inserting the first patient positioner from a front side of the MRI scanner and removing a second patient positioner from between the gap includes removing the second patient positioner from a back side of the MRI scanner.

8. A method of positioning a patient within a gap formed by vertical pole surfaces in an MRI scanner, the method comprising:
   selecting a first patient positioner;
   inserting the first patient positioner into the gap between the vertical pole surfaces; and
   adjusting the position of a patient using the first patient positioner, wherein adjusting the position of a patient includes rotating a platform on the first patient positioner relative to a frame of the first patient positioner, and wherein rotating the platform on the first patient positioner relative to the frame includes raising and lowering a second end of the platform relative to a first end of the platform.

9. A method of positioning a patient within a gap formed by vertical pole surfaces in an MRI scanner, the method comprising:

selecting a first patient positioner;

inserting the first patient positioner into the gap between the vertical pole surfaces;

adjusting the position of a patient using the first patient positioner, wherein adjusting the position of a patient includes rotating a back rest portion on the first patient positioner relative to a base on the first patient positioner and rotating a lower section relative to the base; and sensing the position of the lower section and the back rest portion, wherein adjusting the position of a patient includes analyzing data received during sensing the position of the lower section and the back rest portion and adjusting the patient positioner based on the data.

10. A method of positioning a patient within a gap formed by vertical pole surfaces in an MRI scanner, the method comprising:

selecting a first patient positioner; and inserting the first patient positioner into the gap between the vertical pole surfaces, wherein inserting the first patient positioner into the gap between the vertical pole surfaces includes placing the first patient positioner onto an elevator and elevating the first patient positioner using the elevator, wherein placing the first patient positioner onto an elevator includes placing the first patient positioner on a support platform and elevating the first patient positioner includes raising the support platform with a scissors mechanism; and sensing a height of the support platform and controlling a height of the elevator based on the sensed height of the support platform.

11. A method of positioning a patient within a gap formed by vertical pole surfaces in an MRI scanner, the method comprising:

selecting a first patient positioner; and inserting the first patient positioner into the gap between the vertical pole surfaces; and exchanging position data relating to different parts of the first positioner between a control and radio frequency (RF) connection ports to orient the first patient positioner.

12. A method of positioning a patient within a gap formed by vertical pole surfaces in an MRI scanner, the method comprising:

selecting a first patient positioner; and inserting the first patient positioner into the gap between the vertical pole surfaces, wherein inserting the first patient positioner into the gap between the vertical pole surfaces includes inserting at least one gate into the gap.

13. A method of positioning a patient within a gap formed by vertical pole surfaces in an MRI scanner, the method comprising:

selecting a first patient positioner; and inserting the first patient positioner into the gap between the vertical pole surfaces, wherein inserting the first patient positioner into the gap between the vertical pole surfaces includes inserting a plurality of rotatable gates into the gap.

14. The method of claim 13 wherein inserting a plurality of rotatable gates into the gap includes inserting the gates into an elevator positioned below the gap.

* * * * *